United States Patent [19]

Hecquet et al.

[11] Patent Number: 6,080,893
[45] Date of Patent: Jun. 27, 2000

[54] PROCESS FOR THE MANUFACTURE OF ACROLEIN FROM PROPYLENE BY A REDOX REACTION AND USE OF A SOLID MIXED OXIDE COMPOSITION AS REDOX SYSTEM IN THE SAID REACTION

[75] Inventors: Gerard Hecquet, Bethune; Jean-Pierre Schirmann, Paris; Michel Simon, Saint-Avold; Gilles Descat, Saint-Avold; Eric Etienne, Saint-Avold, all of France

[73] Assignee: Elf Atochem, S.A., Paris-la-Defense, France

[21] Appl. No.: 09/031,665

[22] Filed: Feb. 27, 1998

[30] Foreign Application Priority Data

Feb. 27, 1997 [FR] France ..................... 97 02343

[51] Int. Cl.⁷ .............. B01J 23/28; B01J 23/18; B01J 23/31; B01J 23/54
[52] U.S. Cl. .................. 568/479; 568/479; 568/477; 502/308; 502/315; 502/316; 502/321; 502/325; 502/352; 502/242; 502/249; 502/255; 502/258; 502/259; 502/260
[58] Field of Search ...................... 568/479, 477; 502/308, 315, 316, 321, 325, 352, 242, 249, 255, 258, 259, 260

[56] References Cited

U.S. PATENT DOCUMENTS

| | | | |
|---|---|---|---|
| 3,968,166 | 7/1976 | Shiraishi et al. ......... | 568/480 |
| 4,018,712 | 4/1977 | Li .......................... | 502/249 |
| 4,341,717 | 7/1982 | Callahan et al. ......... | 260/465.3 |
| 5,689,005 | 11/1997 | Hagemeyer et al. ...... | 564/420 |
| 5,700,752 | 12/1997 | Kurimoto et al. ........ | 502/311 |

FOREIGN PATENT DOCUMENTS

| | | | |
|---|---|---|---|
| 0 169 449 | 1/1986 | European Pat. Off. ...... | B01J 23/92 |
| 0 450 596 | 10/1991 | European Pat. Off. ...... | C07C 45/35 |
| 2 725 715 | 4/1996 | France ..................... | C07B 35/04 |

*Primary Examiner*—Ralph Gitomer
*Assistant Examiner*—Marjorle A. Moran
*Attorney, Agent, or Firm*—Millen, White, Zelano & Branigan, P.C.

[57] ABSTRACT

A mixed oxide solid composition of formula (I):

$$Mo_{12}W_aBi_bFe_cCo_dNi_eSi_fK_gSn_hO_x \qquad (I)$$

where $0 \leq a \leq 5$, $0.5 \leq b \leq 5$, $0.1 \leq c \leq 10$, $0.5 \leq d \leq 10$, $0 \leq e \leq 10$, $0 \leq f \leq 15$, $0 \leq g \leq 1$, $0 \leq h \leq 2$ and x is the quantity of oxygen bonded to the other elements and depends on their oxidation states, is used in the manufacture of acrolein by oxidizing propylene, the solid composition reacting with propylene according to the redox reaction (1):

$$solid_{oxidized} + propylene \rightarrow solid_{reduced} + acrolein \qquad (I)$$

To manufacture acrolein, gaseous propylene is passed over a solid composition of formula (I), to conduct the redox reaction (1) by operating at a temperature of 200 to 600° C., at a pressure of $1.01 \times 10^4$ to 1.01 to $10^6$ Pa (0.1 to 10 atmospheres) and with a residence time of 0.01 second to 90 seconds, in the absence of molecular oxygen.

16 Claims, No Drawings

PROCESS FOR THE MANUFACTURE OF ACROLEIN FROM PROPYLENE BY A REDOX REACTION AND USE OF A SOLID MIXED OXIDE COMPOSITION AS REDOX SYSTEM IN THE SAID REACTION

The present invention relates to the manufacture of acrolein from propylene by oxidation according to a redox reaction. The invention also relates to the use of a solid mixed oxide composition as redox system in the said reaction.

BACKGROUND OF THE INVENTION

At the present time acrolein is industrially produced by vapour phase catalytic oxidation of propylene. All the attempts to improve this process have hitherto been concerned with the development of catalysts which give the highest possible conversion of propylene and the highest possible selectivity for the desired acrolein.

Thus, French Patent No. 2 093 773 describes the manufacture of acrolein by vapour phase catalytic oxidation of propylene with molecular oxygen in the presence of an oxide catalyst in which the composition of the catalytic elements, expressed as atomic ratio, is the following:

$Co_{2.0-20.0}Fe_{0.1-10.0}Bi_{0.1-10.0}W_{0.5-10.0}Mo_{2.0-11.5}Si_{0.5-15.0}Z_{0.005-1.0}$ with W+Mo=12.0 and Z denoting an alkali metal. This catalyst can be prepared by mixing aqueous solutions of ammonium molybdate and of ammonium paratungstate, adding solutions of cobalt nitrate, of iron nitrate and of bismuth nitrate to the aqueous mixture and then adding an aqueous solution of an alkali metal hydroxide or carbonate and then colloidal silica as a source of silicon, by moulding the substance obtained and by calcining it at 350–600° C. in a stream of air.

U.S. Pat. No. 3,855,308 describes the preparation of acrolein by vapour phase catalytic oxidation of propylene with molecular oxygen in the presence of an oxide catalyst in which the composition of the catalytic elements, expressed as atomic ratio, is the following:

$Co_{2.0-20.0}Fe_{0.1-10.0}Bi_{0.1-10.0}W_{0.5-10.0}Mo_{2.0-11.5}Si_{0.5-15.0}Tl_{0.005-3.0}Z_{0-3.0}$ with W+Mo=12.0 and Z denoting an alkali metal or alkaline-earth metal. The raw materials employed for forming the catalyst may be the oxides of the various metals, but also, depending on circumstances, the nitrates, carbonates or hydroxides. In the case of Mo and W, the salts of acids, such as ammonium molybdate and ammonium tungstate, are recommended. Thus, according to this US patent a catalyst is prepared by mixing aqueous solutions of ammonium molybdate and of ammonium paratungstate respectively, by adding solutions of cobalt nitrate, of iron nitrate and of bismuth nitrate respectively, and then an aqueous solution of alkali metal hydroxide or carbonate and then colloidal silica as a source of silicon, by concentrating the system by evaporation, by adding a support if necessary and by following with an evaporation, a mixing of the resulting substance and a calcination at 350–600° C.

Japanese Patent Showa 45-125 359 describes a vapour phase process for the manufacture of acrolein by catalytic oxidation of propylene with air or oxygen in the presence of a catalyst of formula:

$Ni_aCo_bFe_cBi_dMe_eH_hMo_fO_g$ in which:

a=0–20, b=0–20 with a+b between 0.5 and 20, c=0.5–8, d=0.1–7, 0<e≦2, h=0–0.3, f=12, g=36–90;

Me is one out of Sn, Zn, W, Cr, Mn and Ti; and

H is at least one out of K, Rb and Cs.

To prepare this catalyst, aqueous solutions of Ni, Co, Fe, K (and/or Rb, Cs), Bi and Me compounds may be added to an aqueous solution of a molybdenum compound (ammonium molybdate, molybdic acid or molybdenum oxide), then a support such as alumina, silicon carbide and silica (silica sol or silica gel) may be added and then the resulting mixture is heated to dryness, is calcined at approximately 500° C. and is converted into pastilles.

SUMMARY OF THE INVENTION

It has now been discovered that acrolein can be manufactured by gas phase oxidation of propylene in the absence of molecular oxygen by passing propylene over a particular solid mixed oxide composition which acts as a redox system and supplies the oxygen necessary for the reaction.

The advantages of this new process are the following:

the limitation of the overoxidation of the products formed, which takes place in the presence of molecular oxygen; according to the present invention, since the operation is carried out in the absence of molecular oxygen, the formation of $CO_x$ (carbon monoxide and carbon dioxide), degradation products, is reduced, and this allows the selectivity for acrolein to be increased, as shown hereinafter by the Comparative Examples 4, 8, 12 and 16;

the selectivity for acrolein remains good when the degree of reduction of the solid composition increases;

once it has undergone a reduction and a gradual loss of its activity, the solid composition can be easily regenerated by heating in the presence of oxygen or of an oxygen-containing gas after a certain period of use; after the regeneration the solid recovers its initial activity and can be employed in a new reaction cycle;

the separation of the stages of reduction of the solid composition and of its regeneration makes it possible:
to increase the selectivity for acrolein; and
to increase the partial pressure of propylene, such a partial pressure of propylene feed no longer being limited by the existence of an explosive region of the propylene + oxygen mixture.

The subject-matter of the present invention is therefore firstly the use of a solid mixed oxide composition of formula (I):

$$Mo_{12}W_aBi_bFe_cCo_dNi_eSi_fK_gSn_hO_x \qquad (I)$$

in which:

a is between 0 and 5, limits included,
b is between 0.5 and 5, limits included,
c is between 0.1 and 10, limits included,
d is between 0.5 and 10, limits included,
e is between 0 and 10, limits included,
f is between 0 and 15, limits included,
g is between 0 and 1, limits included,
h is between 0 and 2, limits included, and
x is the quantity of oxygen bonded to the other elements and depends on their oxidation states, in the manufacture of acrolein by propylene oxidation, the said solid composition reacting with the propylene according to the redox reaction (1):

$$\text{solid}_{oxidized}+\text{propylene} \rightarrow \text{solid}_{reduced}+\text{acrolein} \qquad (1).$$

The oxides of the various metals forming part of the composition of the mixed oxide of formula (I) can be employed as raw materials in the preparation of this composition, but the raw materials are not restricted to the oxides; other raw materials which may be mentioned are:

- in the case of molybdenum, ammonium molybdate and molybdic acid and, in the case of tungsten, ammonium tungstate and tungstic acid,
- in the case of cobalt, bismuth, nickel and iron, the nitrates, carbonates and hydroxides, such as cobalt nitrate, bismuth nitrate, nickel nitrate and ferric nitrate,
- in the case of tin, tin chloride and tin hydroxide, and
- in the case of potassium, potassium hydroxide, carbonate or nitrate, and, in general, any compounds capable of forming an oxide by calcination, namely metal salts of organic acids, metal salts of inorganic acids, metal complex compounds, organometallic compounds and the like.

The source of silicon generally consists of colloidal silica.

The subject-matter of the present invention is a process for the manufacture of acrolein from propylene, according to which process gaseous propylene is passed over a solid composition of formula (I) as defined above, to conduct the redox reaction (1) as indicated above, while operating at a temperature of 200 to 600° C., especially from 250 to 450° C., at a pressure of $1.01 \times 10^4$ to $1.01 \times 10^6$ Pa (0.1 to 10 atmospheres), especially of $5.05 \times 10^4$ to $5.05 \times 10^5$ Pa (0.5–5 atmospheres), and with a residence time of 0.01 second to 90 seconds, especially of 0.1 second to 30 seconds, in the absence of molecular oxygen.

In accordance with particular embodiments of the present invention the gaseous propylene may be introduced as a mixture with an inert gas such as nitrogen and/or with water (water vapour).

During the redox reaction (1) the solid composition undergoes a reduction and a progressive loss of its activity. This is why, once the solid composition has changed to the reduced state, regeneration of the said solid composition is conducted according to reaction (2):

$$\text{solid}_{reduced} + O_2 \rightarrow \text{solid}_{oxidized} \qquad (2)$$

by heating in the presence of an excess of oxygen or of an oxygen-containing gas at a temperature of 250 to 500° C., for the time necessary for the reoxidation of the solid composition.

After the regeneration, which may be performed in temperature and pressure conditions that are identical with or different from those of the redox reaction, the solid composition recovers an initial activity and can be employed in a new reaction cycle.

The redox reaction (1) and the regeneration can be conducted in a two-stage device, namely a reactor and a regenerator which function simultaneously and in which two charges of solid composition alternate periodically; the redox reaction (1) and the regeneration can also be conducted in the same reactor by alternating the reaction and regeneration periods.

The preparation of acrolein according to the invention is performed according to a stoichiometric and not catalytic reaction.

The following examples illustrate the present invention without, however, limiting its scope. In the formulae shown in these examples x is the quantity of oxygen bonded to the other elements and depends on their oxidation states.

The conversions, selectivities and yields are defined as follows:

conversion(%) =

$$\frac{\text{number of moles of propulene which have reacted}}{\text{number of moles of propylene introduced}} \times 100$$

selectivity for acrolein(%) =

$$\frac{\text{number of moles of acrylic acid formed}}{\text{number of moles of propylene which have reacted}} \times 100$$

selectivity for acrylic acrylicacid (%) =

$$\frac{\text{number of moles of acrylic acid formed}}{\text{number of moles of propylene which have reacted}} \times 100$$

EXAMPLE 1

(a) Preparation of a Solid of Formula

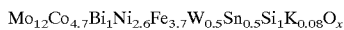

$Mo_{12}Co_{4.7}Bi_1Ni_{2.6}Fe_{3.7}W_{0.5}Sn_{0.5}Si_1K_{0.08}O_x$ 618 g of $Co(NO_3)_2 \cdot 6H_2O$, 343 g of $Ni(NO_3)_2 \cdot 6H_2O$, 674 g of $Fe(NO_3)_3 \cdot 9H_2O$ and 3.8 g of $KNO_3$ are dissolved in 1250 ml of distilled water at ambient temperature. 230 g of $Bi(NO_3)_3 \cdot 5H_2O$ are dissolved, also at ambient temperature, in 300 ml of distilled water acidified with 50 ml of $HNO_3$ at a concentration of 68% by volume. 53 g of $SnCl_2 \cdot 2H_2O$ are dissolved in 60 ml of distilled water, also at ambient temperature. 956.2 g of $(NH_4)_6Mo_7O_{24} \cdot 4H_2O$ are dissolved in 2600 ml of distilled water at 40° C.

The solution containing the bismuth and that containing the tin are poured successively, with stirring, into the solution containing Co, Ni, Fe and K. The resulting solution is next poured, still with stirring, into the solution containing the molybdenum. 71 g of colloidal silica (at a concentration of 40 mass %) and 55.6 g of $WO_3$ are then sprinkled into it. The resulting mixture is heated to 90° C. for 1.5 hours and is then dried for 12 hours at 140° C. The solid obtained is calcined for 6 hours at 500° C. in air. The various metals are present in this solid in the atomic ratios shown in the title of this example.

(b) Preparation of Acrolein From Propylene By Redox Reaction 200 mg of this solid are charged into a tubular reactor at 400° C. and are then purged with a continuous stream of 12 ml/min of helium. $2.3 \times 10^{-6}$ mol of propylene are injected onto the solid. The propylene conversion is 91.5%, with selectivities for acrolein and acrylic acid of 80.0% and 4.0% respectively.

EXAMPLE 2

After the reaction of Example 1 (b) has been conducted, the same solid is subjected again to four successive propylene injections in the same test conditions as in Example 1. The performances obtained are reported in Table 1.

TABLE 1

| Injection No. | Propylene conversion (%) | Selectivity for acrolein (%) | Selectivity for acrylic acid (%) |
|---|---|---|---|
| 1 | 89.4 | 81.0 | 4.0 |
| 2 | 87.3 | 79.1 | 3.8 |
| 3 | 85.5 | 80.1 | 3.8 |
| 4 | 83.7 | 78.9 | 3.7 |

EXAMPLE 3

After the reducing treatment of Example 2 the solid is regenerated for 1 hour in air at 400° C. and then replaced under a flow of helium. Four successive new injections of $2.3 \times 10^{-6}$ mol of propylene are directed onto the solid. The performances obtained are reported in Table 2.

TABLE 2

| Injection No. | Propylene conversion (%) | Selectivity for acrolein (%) | Selectivity for acrylic acid (%) |
| --- | --- | --- | --- |
| 1 | 93.3 | 80.7 | 4.4 |
| 2 | 90.6 | 81.0 | 4.2 |
| 3 | 88.2 | 80.4 | 4.0 |
| 4 | 86.0 | 80.0 | 3.9 |

EXAMPLE 4 (comparative)

200 mg of a solid prepared according to Example 1 are charged into a tubular reactor at 400° C. and are then purged with a continuous flow of 12 ml/min of air. $2.3 \times 10^{-6}$ mol of propylene are injected onto the solid. The propylene conversion is 92.9% with selectivities for acrolein and acrylic acid of 70.4% and 3.4% respectively.

EXAMPLE 5

(a) Preparation of a Solid of Formula $$Mo_{12}Co_{3.5}Bi_{1.1}Fe_{0.8}W_{0.5}Si_{1.4}K_{0.05}O_x$$

60.9 g of $Co(NO_3)_2 \cdot 6H_2O$ are dissolved in 20 ml of distilled water.

20.2 g of $Fe(NO_3)_3 \cdot 9H_2O$ are also dissolved in 15 ml of distilled water, and 31.2 g of $Bi(NO_3)_3 \cdot 5H_2O$ in 30 ml of distilled water acidified with 6 ml $HNO_3$ at a concentration of 68% by volume.

127.4 g of $(NH_4)_6Mo_7O_{24} \cdot 4H_2O$ are dissolved separately in 150 ml of water with heating and stirring and then 7.4 g of $WO_3$ are added.

The aqueous solution containing the cobalt is introduced dropwise over 20 minutes into the aqueous solution of the ammonium salts. The ferric solution is next introduced over 10 minutes and then the solution containing the bismuth over 15 minutes. A solution obtained by dissolving 0.2 g of KOH and 12.8 g of colloidal silica (at a concentration of 40 mass %) in 15 ml of water is added over 10 minutes to the resulting gel. The gel thus obtained is blended for 1 hour at ambient temperature and then 1 hour at 70° C.

The gel is next dried for 18 hours at 130° C. The solid obtained is calcined for 9 hours at 450° C. in air. The various metals are present in this solid in the atomic ratios as shown in the title of the example.

(b) Preparation of Acrolein From Propylene By Redox Reaction 200 mg of this solid are charged into a tubular reactor at 400° C. and then purged with a continuous flow of 12 ml/min of helium. $2.3 \times 10^{-6}$ mol of propylene are injected onto the solid. The propylene conversion is 82.8% with selectivities for acrolein and acrylic acid of 77.7% and 5.1% respectively.

EXAMPLE 6

After the reaction of Example 5 (b) has been conducted, the same solid is again subjected to four successive propylene injections in the same test conditions as Example 5. The performances obtained are reported in Table 3.

TABLE 3

| Injection No. | Propylene conversion (%) | Selectivity for acrolein (%) | Selectivity for acrylic acid (%) |
| --- | --- | --- | --- |
| 1 | 79.8 | 77.8 | 5.1 |
| 2 | 75.4 | 76.5 | 4.8 |
| 3 | 72.0 | 75.7 | 4.5 |
| 4 | 69.3 | 75.4 | 4.6 |

EXAMPLE 7

After the reducing treatment of Example 6 the solid is regenerated for 1 hour in air at 400° C. and then replaced under a flow of helium. Four new injections of $2.3 \times 10^{-6}$ mol of propylene are directed onto the solid. The performances obtained are reported in Table 4.

TABLE 4

| Injection No. | Propylene conversion (%) | Selectivity for acrolein (%) | Selectivity for acrylic acid (%) |
| --- | --- | --- | --- |
| 1 | 83.9 | 78.5 | 5.6 |
| 2 | 77.7 | 77.9 | 5.2 |
| 3 | 72.6 | 76.2 | 4.6 |
| 4 | 69.5 | 74.7 | 4.4 |

EXAMPLE 8 (comparative)

200 mg of a solid prepared according to Example 5 are charged into a tubular reactor at 400° C. and are then purged with a continuous flow of 12 ml/min of air. $2.3 \times 10^{-6}$ mol of propylene are injected onto the solid. The propylene conversion is 84.9% with selectivities for acrolein and acrylic acid of 66.1% and 5.0% respectively.

EXAMPLE 9

(a) Preparation of a Solid of Formula $$Mo_{12}Co_{3.5}Bi_{1.1}Fe_{0.8}W_{0.5}Si_{1.4}K_{0.05}O_x$$

The above solid is prepared in the same way as in Example 5 but with the 7.4 g of $WO_3$ replaced with 8.1 g of ammonium paratungstate.

(b) Preparation of Acrolein From Propylene By Redox Reaction

This solid is employed for the reaction of Example 5 with the following results: the propylene conversion is 92.1%, with selectivities for acrolein and acrylic acid of 72.7% and 8.0% respectively.

EXAMPLE 10

After the reaction of Example 9 (b) has been conducted, the same solid is again subjected to four successive injections of propylene in the same test conditions as in Example 9. The performances obtained are reported in Table 5.

TABLE 5

| Injection No. | Propylene conversion (%) | Selectivity for acrolein (%) | Selectivity for acrylic acid (%) |
| --- | --- | --- | --- |
| 1 | 89.8 | 72.4 | 7.4 |
| 2 | 86.4 | 73.6 | 7.0 |

TABLE 5-continued

| Injection No. | Propylene conversion (%) | Selectivity for acrolein (%) | Selectivity for acrylic acid (%) |
|---|---|---|---|
| 3 | 83.7 | 71.2 | 6.7 |
| 4 | 80.5 | 70.7 | 6.3 |

EXAMPLE 11

After the reducing treatment of Example 10 the solid is regenerated for 1 hour in air at 400° C. and then replaced under a flow of helium. Four successive new injections of $2.3\times10^{-6}$ mol of propylene are directed onto the solid. The performances obtained are reported in Table 6.

TABLE 6

| Injection No. | Propylene conversion (%) | Selectivity for acrolein (%) | Selectivity for acrylic acid (%) |
|---|---|---|---|
| 1 | 90.7 | 73.4 | 7.8 |
| 2 | 87.2 | 74.3 | 7.1 |
| 3 | 83.3 | 72.4 | 6.5 |
| 4 | 80.3 | 70.7 | 6.2 |

EXAMPLE 12 (comparative)

200 mg of a solid prepared according to Example 9 are charged into a tubular reactor at 400° C. and are then purged with a continuous flow of 12 mi/min of air. $2.3\times10^{-6}$ mol of propylene are injected onto the solid. The propylene conversion is 91.3% with selectivities for acrolein and acrylic acid of 61.0% and 6.9% respectively.

EXAMPLE 13
(a) Preparation of a Solid of Formula

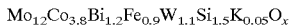

$Mo_{12}Co_{3.8}Bi_{1.2}Fe_{0.9}W_{1.1}Si_{1.5}K_{0.05}O_x$

The above solid is prepared in the same way as in Example 5.
(b) Preparation of Acrolein From Propylene By Redox Reaction This solid is employed for the reaction of Example 5 with the following results: the propylene conversion is 90.4% with selectivities for acrolein and acrylic acid of 78.1% and 6.3% respectively.

EXAMPLE 14

After the reaction of Example 13 (b) has been conducted, the same solid is again subjected to four successive injections of propylene in the same test conditions as in Example 13. The performances obtained are reported in Table 7.

TABLE 7

| Injection No. | Propylene conversion (%) | Selectivity for acrolein (%) | Selectivity for acrylic acid (%) |
|---|---|---|---|
| 1 | 85.0 | 78.7 | 5.3 |
| 2 | 80.9 | 78.0 | 4.9 |
| 3 | 76.8 | 77.5 | 4.8 |
| 4 | 73.4 | 76.9 | 4.5 |

EXAMPLE 15

After the reducing treatment of Example 14, the solid is regenerated for 1 hour in air at 400° C. and then replaced under a flow of helium. Four new injections of $2.3\times10^{-6}$ mol of propylene are directed onto the solid. The performance obtained are reported in Table 8.

TABLE 8

| Injection No. | Propylene conversion (%) | Selectivity for acrolein (%) | Selectivity for acrylic acid (%) |
|---|---|---|---|
| 1 | 91.3 | 78.1 | 7.7 |
| 2 | 88.7 | 79.6 | 6.3 |
| 3 | 84.6 | 78.3 | 5.3 |
| 4 | 80.2 | 78.3 | 4.8 |

EXAMPLE 16 (comparative)

200 mg of a solid prepared according to Example 9 are charged into a tubular reactor at 400° C. and are then purged with a continuous flow of 12 ml/min of air. $2.3\times10^{-6}$ mol of propylene are injected onto the solid. The propylene conversion is 91.8% with selectivities for acrolein and acrylic acid of 71.0% and 6.6% respectively.

The preceding examples can be repeated with similar success by substituting the generically or specifically described reactants and/or operating conditions of this invention for those used in the preceding examples.

The entire disclosure of all applications, patents and publications, cited above and below, and of corresponding French application No. 97/02343, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

As for the expression "in the substantial absence of molecular oxygen" in the claims, it is to be understood that the greater the removal of oxygen from the reactor prior to the reaction, the better the selectivity to acrolein will be. However, a chemical engineer will readily recognize that the extent of removal of molecular oxygen is a cost/benefit problem. For example, it might be very expensive to remove final traces of molecular oxygen to obtain only a slight improvement. Thus, the word "substantial" is intended to convey an absence of molecular oxygen which leads to an improved result as compared to a process where no effort is made to eliminate molecular oxygen, for example those processes set forth in the comparative examples.

We claim:

1. A process for the manufacture of acrolein from propylene according to the redox reaction (1):

$solid_{oxidated}$+propylene→$solid_{reduced}$+acrolein (1), said process comprising reacting gaseous propylene with said oxidated solid which has a composition of formula (I):

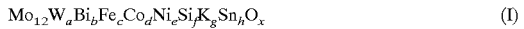

$Mo_{12}W_aBi_bFe_cCo_dNi_eSi_fK_gSn_hO_x$ (I)

in which:
a is between 0 and 5, limits included,
b is between 0.5 and 5, limits included,
c is between 0.1 and 10, limits included,
d is between 0.5 and 10, limits included,
e is between 0 and 10, limits included,
f is between 0 and 15, limits included,
g is between 0 and 1, limits included, h is between 0 and 2, limits included, and x is the quantity of oxygen bonded to the other elements and depends on their oxidation states, at a temperature of 200 to 600° C., at a pressure of $1.01 \times 10^4$ to $1.01 \times 10^6$ Pa and with a reaction time of 0.01 second to 90 seconds, in the substantial absence of molecular oxygen.

2. A process according to claim 1, wherein the gaseous propylene is introduced as a mixture with an inert gas.

3. A process according to claim 1, wherein the redox reaction (1) is conducted at a temperature of 250 to 450° C.

4. A process according to claim 2, wherein the redox reaction (1) is conducted at a temperature of 250 to 450° C.

5. A process according to claim 2, wherein the redox reaction (1) is conducted at a pressure of $5.05 \times 10^4$–$5.05 \times 10^5$ Pa.

6. A process according to claim 3, wherein the redox reaction (1) is conducted at a pressure of $5.05 \times 10^4$–$5.05 \times 10^5$ Pa.

7. A process according to claim 2, wherein the redox reaction (1) is conducted with a reaction time of 0.1 second to 30 seconds.

8. A process according to claim 6, wherein the redox reaction (1) is conducted with a reaction time of 0.1 second to 30 seconds.

9. A process according to claim 1, further comprising regenerating said solid composition according to reaction (2):

$$\text{solid}_{reduced} + O_2 \rightarrow \text{solid}_{oxidized} \qquad (2)$$

by heating the reduced solid in the presence of an excess of oxygen or of an oxygen-containing gas at a temperature of 250 to 500° C., for the time necessary for reoxidizing of the solid composition.

10. A process according to claim 9, wherein the redox reaction (1) and the regeneration are conducted in a two-stage device comprising a reactor and a regenerator which function simultaneously and in which two charges of solid composition alternate periodically.

11. A process according to claim 9, wherein the redox reaction (1) and the regeneration are conducted in the same reactor by alternating the reaction and regeneration periods.

12. A process according to claim 1, further comprising prior to the reaction, introducing the solid composition into a reactor and purging the reactor with an inert gas to deplete the reactor of oxygen.

13. A process according to claim 2, wherein the inert gas is helium.

14. A process according to claim 1, wherein:

(a) is 0.05–1.1; (b) is 1–1.2; (c) is 0.8–3.7;

(d) is 3.5–4.7; (f) is 1–1.5; and (g) is 0.05–0.08.

15. A process according to claim 1 conducted in the complete absence of molecular oxygen.

16. A process according to claim 1, wherein the solid composition is selected from the group consisting of (a) $Mo_{12}Co_{4.7}Bi_1Ni_{2.6}Fe_{3.7}W_{0.5}Sn_{0.5}Si_1K_{0.08}O_x$ and (b) $Mo_{12}Co_{3.5}Bi_{1.1}Fe_{0.8}W_{0.5}Si_{1.4}K_{0.05}O_x$, wherein x is the quantity of oxygen bonded to the other elements and depends on their oxidation states.

* * * * *